United States Patent
Olson

(10) Patent No.: US 9,549,689 B2
(45) Date of Patent: Jan. 24, 2017

(54) SYSTEM AND METHOD FOR CORRECTION OF INHOMOGENEOUS FIELDS

(75) Inventor: Eric S. Olson, Maplewood, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 2960 days.

(21) Appl. No.: 11/715,919

(22) Filed: Mar. 9, 2007

(65) Prior Publication Data

US 2008/0221643 A1  Sep. 11, 2008

(51) Int. Cl.
*A61N 1/00* (2006.01)
*A61B 5/06* (2006.01)
(Continued)

(52) U.S. Cl.
CPC ............... *A61B 5/06* (2013.01); *A61B 34/20* (2016.02); *A61B 90/36* (2016.02); *A61B 5/0422* (2013.01); *A61B 6/503* (2013.01); *A61B 34/10* (2016.02); *A61B 90/90* (2016.02); *A61B 2017/00053* (2013.01); *A61B 2017/00243* (2013.01); *A61B 2017/00482* (2013.01); *A61B 2017/00703* (2013.01); *A61B 2017/00725* (2013.01); *A61B 2034/105* (2016.02); *A61B 2034/2051* (2016.02); *A61B 2034/2053* (2016.02); *A61B 2090/364* (2016.02)

(58) Field of Classification Search
CPC ........... A61B 34/20; A61B 90/36; A61B 5/06; A61B 5/0422; A61B 6/503; A61B 2017/00053; A61B 2017/00243; A61B 2017/00482; A61B 2017/00703; A61B 2017/00725
USPC .......... 600/424, 426, 434, 509; 607/60, 161; 382/131, 184; 128/898, 899; 702/19
See application file for complete search history.

(56) References Cited

U.S. PATENT DOCUMENTS 5,297,549 A   3/1994   Beatty et al.
5,391,199 A   2/1995   Ben-Haim
(Continued)

FOREIGN PATENT DOCUMENTS

EP   1757227   2/2007
JP   03-099630   4/1991
(Continued)

OTHER PUBLICATIONS

Orr, Mark J , "Introduction to radial basis function networks", *Article* Apr. 1996.
(Continued)

*Primary Examiner* — Joseph M Santos Rodriguez
(74) *Attorney, Agent, or Firm* — Wiley Rein LLP

(57) ABSTRACT

A method for determining a location of an object in a three-dimensional localization field created by a localization system includes the following steps: providing a catheter having known spacing between electrodes; providing a lookup table of data correlating locations of an object within the localization field with measurements made by the localization system; placing the catheter into the localization field; using the localization system to determine the location of the electrodes based on the lookup table; calculating an observed distance between electrodes; comparing the observed distance to the known electrode spacing; and adjusting the lookup table to more accurately measure the spacing of the electrodes. A Kernel function, such as the derivative of a Gaussian function, may be used to update the lookup table.

18 Claims, 6 Drawing Sheets

(51) Int. Cl.
*A61B 5/042* (2006.01)
*A61B 6/00* (2006.01)
*A61B 17/00* (2006.01)

(56) References Cited

U.S. PATENT DOCUMENTS

| | | | |
|---|---|---|---|
| 5,480,422 | A | 1/1996 | Ben-Haim |
| 5,546,951 | A | 8/1996 | Ben-Haim |
| 5,568,809 | A | 10/1996 | Ben-Haim |
| 5,662,108 | A | 9/1997 | Budd et al. |
| 5,694,945 | A | 12/1997 | Ben-Haim |
| 5,697,377 | A | 12/1997 | Wittkampf |
| 5,718,241 | A | 2/1998 | Ben-Haim et al. |
| 5,738,096 | A | 4/1998 | Ben-Haim |
| 5,840,025 | A | 11/1998 | Ben-Haim |
| 5,944,022 | A | 8/1999 | Nardella et al. |
| 5,954,665 | A | 9/1999 | Ben-Haim |
| 5,983,126 | A | 11/1999 | Wittkampf |
| 6,016,439 | A | 1/2000 | Acker |
| 6,066,094 | A | 5/2000 | Ben-Haim |
| 6,104,944 | A | 8/2000 | Martinelli |
| 6,161,032 | A | 12/2000 | Acker |
| 6,226,542 | B1 | 5/2001 | Reisfeld |
| 6,468,265 | B1 | 10/2002 | Evans et al. |
| 6,640,119 | B1 | 10/2003 | Budd et al. |
| 6,728,562 | B1 | 4/2004 | Budd et al. |
| 6,939,309 | B1 | 9/2005 | Beatty et al. |
| 6,947,785 | B1 | 9/2005 | Beatty et al. |
| 6,978,168 | B2 | 12/2005 | Beatty et al. |
| 6,990,370 | B1 | 1/2006 | Beatty et al. |
| 7,263,397 | B2 | 8/2007 | Hauck et al. |
| 2002/0115941 | A1* | 8/2002 | Whayne et al. ............. 600/523 |
| 2002/0168618 | A1 | 11/2002 | Anderson et al. |
| 2003/0021381 | A1 | 1/2003 | Koppe et al. |
| 2003/0053697 | A1* | 3/2003 | Aylward et al. ............. 382/203 |
| 2003/0233037 | A1 | 12/2003 | Bencini |
| 2004/0097806 | A1 | 5/2004 | Hunter et al. |
| 2004/0138548 | A1 | 7/2004 | Strommer et al. |
| 2004/0254437 | A1 | 12/2004 | Hauck et al. |
| 2004/0258887 | A1 | 12/2004 | Maciag et al. |
| 2005/0080328 | A1 | 4/2005 | Vass et al. |
| 2005/0137478 | A1 | 6/2005 | Younge et al. |
| 2005/0197568 | A1 | 9/2005 | Vass et al. |
| 2005/0222554 | A1 | 10/2005 | Wallace et al. |
| 2005/0244042 | A1 | 11/2005 | Sirohey et al. |
| 2006/0078195 | A1 | 4/2006 | Vaillant et al. |
| 2006/0079759 | A1 | 4/2006 | Vaillant et al. |
| 2006/0084867 | A1 | 4/2006 | Tremblay et al. |
| 2006/0095022 | A1 | 5/2006 | Moll et al. |
| 2006/0100610 | A1 | 5/2006 | Wallace et al. |
| 2006/0116575 | A1 | 6/2006 | Willis |
| 2006/0210147 | A1 | 9/2006 | Sakaguchi |
| 2006/0253031 | A1 | 11/2006 | Altmann et al. |
| 2007/0003123 | A1 | 1/2007 | Fu et al. |
| 2007/0055142 | A1 | 3/2007 | Webler |
| 2007/0060833 | A1 | 3/2007 | Hauck |
| 2007/0167801 | A1 | 7/2007 | Webler et al. |
| 2007/0181139 | A1 | 8/2007 | Hauck |
| 2007/0223794 | A1 | 9/2007 | Preiss et al. |
| 2007/0297657 | A1 | 12/2007 | Mattes et al. |

FOREIGN PATENT DOCUMENTS

| | | |
|---|---|---|
| JP | 1996/131403 | 5/1996 |
| JP | H08-131403 | 5/1996 |
| JP | 2002-153443 | 5/2002 |
| JP | 2004-209262 | 7/2004 |
| JP | 2005/078176 | 3/2005 |
| JP | 2005-131367 | 5/2005 |
| JP | 11743575 | 1/2007 |
| KG | 10-149445 | 6/1998 |
| WO | 98/19619 | 5/1998 |
| WO | 00/33723 | 6/2000 |
| WO | 02082375 | 10/2002 |
| WO | WO-2006/026177 | 3/2006 |
| WO | 2008/112420 | 9/2008 |

OTHER PUBLICATIONS

International Search Report and Written Opinion of the International Searching Authority for PCT/US07/89198 filed Dec. 31, 2007, dated Jul. 22, 2008.

U.S. Appl. No. 11/715,923, filed Mar. 9, 2007, Olson.

Bookstein, FL., Principal Warps: Thin Plate Splines and the Decomposition of Deformations, IEEE Transactions on Pattern Analysis and Machine Intelligence, 11:567-585 (1989).

Bookstein, FL., Thin-Plate Splines and the Atlas Problem for Biomedical Images, Proceedings of the 12th International Conference on Information Processing in Medical Imaging (Jul. 1991). (abstract).

Schaefer & Warren, Mean Value Coordinates for Closed Triangular Meshes, ACM Transactions on Graphics, 24 (3):561-66 (Jul. 2005).

Park & Sanberg, "Universal approximation using radial-basis-function networks," Neural Computation, 3(2): 246-257 (1991). (abstract).

Bors & Pitas, "Median Radial Basis Function Neural Network," IEEE Trans, On Neural Networks, vol. 7, No. 6, pp. 1351-1364 (Nov. 1996).

"Supplementary European Search Report", EP 07870126 Dec. 19, 2011.

Ameet Kumar Jain; "FTRAC—A robust fluoroscope tracking fiducial"; Medical Physics; vol. 32; No. 10; pp. 3185-3198; Oct. 2005

Haili Chui; "A new algorithm for non-rigid point matching"; IEEE Conference on Computer Vision and Pattern; vol. 2; pp. 44-51; Jun. 2000.

Tao Ju; "Mean Value Coordinates for Closed Triangular Meshes"; ACM Transactions on Graphics 24(3); pp. 561-566; Jul. 2005.

H. Ebeling; "ASMOOTH: A simple and efficient algorithm for adaptive kernel smoothing of two-dimensional imaging data"; Mon. Not. R. Astron, Soc.; vol. 363; pp. 65-73; Mar. 2006.

M.A. Wirth et al., "Point-to-point registration of non-rigid medical images using local elastic transformation methods", Image Processing and its Applications, 1997, Sixth International Conference, vol. 2; pp. 780-794, Jul. 14, 1997.

H.J. Johnson et al., "Consistent landmark and intensity-based image registration"; IEEE Transactions on Medical Imaging, vol. 21, No. 5, pp. 450-461, May 2002.

K. Rohr et al., "Landmark-based elastic registration using approximating thin-plate splines", IEEE Transactions on Imaging, vol. 20, No. 6,pp. 526-534, Jun. 2001.

Martin Auer et al., "An Automatic Nonrigid Registration for Stained Histological Sections", IEEE Transactions on Image Processing, vol. 14, No. 4, pp. 475-486, Apr. 2005.

Xian-yi cheng et al., "Design and realization of medical image nonrigid maching algorithm", Procedings of the Sixth International Conference on Intelligent Systems Design and Applications (ISDA '06), Oct. 2006.

John Moody et al.; "Fast Learning in Networks of Locally-Tuned Processing Units"; Neural Computation; vol. 1; No. 2; pp. 281-294; Jun. 1989.

David F. Wiley et al.; "Evolutionary Morphing"; VLS 05. IEEE Visualization; Oct. 2005.

\* cited by examiner

| | VOLTAGE MEASURED ON X-AXIS | | | | | | | | | |
|---|---|---|---|---|---|---|---|---|---|---|
| | | 0 | 1 | 2 | 3 | 4 | 5 | 6 | 7 | 8 | 9 |
| VOLTAGE MEASURED ON Y-AXIS | 0 | (-3,-5) | (-2,-5) | (-1,-5) | (0,-5) | (1,-5) | (2,-5) | (3,-5) | (4,-5) | (5,-5) | (6,-5) |
| | 1 | (-3,-4) | (-2,-4) | (-1,-4) | (0,-4) | (1,-4) | (2,-4) | (3,-4) | (4,-4) | (5,-4) | (6,-4) |
| | 2 | (-3,-3) | (-2,-3) | (-1,-3) | (0,-3) | (1,-3) | (2,-3) | (3,-3) | (4,-3) | (5,-3) | (6,-3) |
| | 3 | (-3,-2) | (-2,-2) | (-2,-2) | (0,-2) | (1,-2) | (2,-2) | (3,-2) | (4,-2) | (5,-2) | (6,-2) |
| | 4 | (-3,-1) | (-2,-1) | (-1,-1) | (0,-1) | (1,-1) | (2,-1) | (3,-1) | (4,-1) | (5,-1) | (6,-1) |
| | 5 | (-3,0) | (-2,0) | (-1,0) | (0,0) | (1,0) | (2,0) | (3,0) | (4,0) | (5,0) | (6,0) |
| | 6 | (-3,1) | (-2,1) | (-1,1) | (0,1) | (1,1) | (2,1) | (3,1) | (4,1) | (5,1) | (6,1) |
| | 7 | (-3,2) | (-2,2) | (-1,2) | (0,2) | (1,2) | (2,2) | (3,2) | (4,2) | (5,2) | (6,2) |
| | 8 | (-3,3) | (-2,3) | (-1,3) | (0,3) | (1,3) | (2,3) | (3,3) | (4,3) | (5,3) | (6,3) |
| | 9 | (-3,4) | (-2,4) | (-1,4) | (0,4) | (1,4) | (2,4) | (3,4) | (4,4) | (5,4) | (6,4) |

FIG. 3

SYSTEM AND METHOD FOR CORRECTION OF INHOMOGENEOUS FIELDS

CROSS-REFERENCE TO RELATED APPLICATIONS

This application is related to application Ser. No. 11/715,923, filed concurrently herewith, which is hereby incorporated by reference as though fully set forth herein.

BACKGROUND OF THE INVENTION a. Field of the Invention

The instant invention relates to localization systems that measure position utilizing localization fields. In particular, the instant invention relates to a system and method to account for inhomogeneity of the localization field.

b. Background Art

It is well known to generate heart chamber geometry in preparation for cardiac diagnostic or therapeutic procedures. Often, a mapping catheter is introduced into the heart chamber of interest and moved around within the heart chamber, either randomly, pseudo-randomly, or according to one or more preset patterns. The three-dimensional coordinates are measured using a localization system (sometimes also referred to as a "mapping system," "navigation system," or "positional feedback system"). The localization system measures the coordinates of the mapping catheter within a localization field, typically by relating a characteristic of the localization field, such as a voltage, experienced by the mapping catheter to a location of the catheter within the field. A similar process may be used to measure the position of any object, such as an ablation catheter or other medical device, within the localization field.

It is known, however, that the localization field may not be homogeneous. That is, as an object moves within the localization field, there may not be a constant relationship between the characteristic and the position of the object within the field. These inhomogeneities potentially reduce the precision and accuracy of the position measurements made by the localization system.

BRIEF SUMMARY OF THE INVENTION

It is therefore desirable to be able to account for inhomogeneities in a localization field.

Disclosed herein is a method for determining a location of an object in a three-dimensional localization field created by a localization system. The method includes the following steps: providing a catheter having a plurality of electrodes, each of which is spaced from an adjacent electrode by a known electrode spacing distance; providing a three-dimensional lookup table for use by the localization system, wherein the table comprises reference data correlating locations of an object within the localization field with measurements made by the localization system when the object is at various locations; placing the catheter into the localization field; using the localization system to determine the location of each of the plurality of electrodes based on the reference data in the three-dimensional lookup table; calculating an observed distance between each pair of adjacent electrodes from the determined locations of each of the plurality of electrodes; comparing the observed distance between at least one pair of adjacent electrodes to the known electrode spacing to determine an error signal; and adjusting the reference data in the three-dimensional lookup table based on the error signal to more accurately measure the spacing of the electrodes. Optionally, an object may be placed in the localization field, preferably in close proximity to the catheter, and the object's location may be determined using the adjusted data in the three-dimensional lookup table.

In some embodiments of the invention, the reference data comprises information that relates voltage readings to physical location within the localization field, and the three-dimensional lookup table may be generated by predicting reference data for a perfectly homogeneous localization field. Typically, a Kernel function will be used to adaptively update the reference data in the three-dimensional lookup table. The Kernel function is preferably a decay function, in that updates to the reference data diminish in magnitude as the adjustment point increases in distance from the locations of the plurality of electrodes. One suitable Kernel function is a derivative of a Gaussian curve having the general form $$K(x) = axe^{-\frac{x^2}{2\sigma^2}}.$$

Also disclosed is a method for locating an object in a defined space, including the steps of: providing a calibration object having a plurality of calibration elements spaced at known spacing distances; defining a three-dimensional coordinate system for a localization field, the coordinate system including a plurality of reference points which serve as references for defining an observed location of an object located in the localization field; placing the calibration object into the localization field; receiving reference information relative to the three-dimensional coordinate system, the reference information providing position information for each of the calibration elements; calculating an observed spacing distance for at least two of the calibration elements; generating a calibration signal based on a comparison of the observed spacing distance and the known spacing distance; placing an object in the localization field; and using the calibration signal to determine the location of the object in the localization field.

Optionally, at least some of the plurality of reference points may be adaptively processed using a Kernel function to create a revised three-dimensional coordinate system such that a difference between the observed spacing distance and the known spacing distance is reduced. For example, if the observed spacing distance is greater than the known spacing distance, the distance separating at least two reference points may be reduced. Likewise, if the observed spacing distance is less than the known spacing distance, the distance separating at least two reference points may be increased. It is also contemplated that the method may include locating an object within the localization field by providing reference information, including position information for the object within the localization field, relative to the revised three-dimensional coordinate system.

The present invention also includes a localization system with error correction for inhomogeneous localization fields. The system includes: at least one localization field generator for creating a localization field that can be used for determining a location of an object within the localization field; at least one detector to measure the characteristics of the localization field generated by the at least one localization field generator; a modeling processor to create a three-dimensional coordinate system for the localization space, the coordinate system including a plurality of reference points that serve as a reference for defining an observed location of an object in the localization space; an error processor to determine differences between observed distances and actual distance; and a correction processor coupled to the modeling processor and the error processor, wherein the correction processor adjusts locations of at least two reference points in the three-dimensional coordinate system to adjust for differences detected by the error processor, such that any difference between an observed distance and an actual distance is reduced. Of course, the correction processor may use a Kernel function to adaptively adjust locations of the at least two reference points, for example by reducing the distance between the at least two reference points when the observed distance is greater than the actual distance and vice versa. The system optionally further includes a calibration tool having a plurality of calibration elements spaced at known distances, such that an observed distance between calibration elements may be compared to an actual distance between calibration elements.

The modeling processor may create a three-dimensional coordinate system that includes a three-dimensional lookup in which the reference points are associated with measurement values that may be measured by the at least one detector. In some embodiments of the invention, the at least one localization field generator includes three pairs of electrodes spaced along three axes, wherein the three pairs of electrodes create three electric fields that can be used to determine location of an object within a localization space. The at least one detector may therefore measure a voltage level associated with each of the three electric fields, and the modeling processor may create a three-dimensional coordinate system including a three-dimensional lookup in which the reference points of the coordinate system are associated with measurement values for each of the three electric fields as measured by the at least one detector. The correction processor may then adjust for inhomogeneities in the three electric fields. Alternatively, the localization field may be a magnetic field, and the at least one detector may include three coils to detect different components of the magnetic field.

In another aspect of the present invention, a method for determining a location of an object in a three-dimensional localization field created by a localization system includes the steps of: providing a plurality of electrodes, each of which is spaced from an adjacent electrode by a known electrode spacing distance; placing the plurality of electrodes into the localization field; determining an observed location for at least two of the electrodes using reference data; calculating an observed distance between the pair of electrodes from the observed locations of the two electrodes; comparing the observed distance between the two electrodes to the known electrode spacing to determine an error signal; and adjusting the reference data to more accurately measure the spacing of the electrodes. The reference data may be adaptively updated using a kernel function, such as a kernel function having a positive lobe with a central maximum and a smooth decay to zero on either side of the central maximum and a negative lobe with a central minimum and a smooth decay to zero on either side of the central minimum. The reference data may be in the form of a lookup table that correlates locations within the localization field to one or more characteristics of the localization field, such as one or more electrical field characteristics or one or more magnetic field characteristics. It is also contemplated that the known electrode spacing may be derived from a catheter table (that is, a table listing known catheters and their known electrode spacings).

An advantage of the present invention is that it provides a localization system that corrects for inhomogeneities in the localization field within which positions are measured.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 3 illustrates a representative lookup table in two dimensions.

DETAILED DESCRIPTION OF THE INVENTION

The present invention provides a method and system for accounting for inhomogeneities in a localization field. Localization fields are often employed in procedures carried out within a human body, and in particular in cardiac diagnostic and therapeutic procedures. Therefore, for purposes of illustration, the invention will be described in detail in the context of a localization system utilized in a cardiac electrophysiology procedure. It is contemplated, however, that the present invention may be practiced to good advantage in other contexts, including, for example, to measure internal distortions in a manufacturing environment. Further, though the invention will generally be illustrated in two-dimensions, one of ordinary skill in the art will appreciate how to apply the principles described herein in any number of dimensions. For example, the present invention may be practiced in the time domain in order to compensate for changes in localization fields that occur with respiration and cardiac motion.

Figure 1:
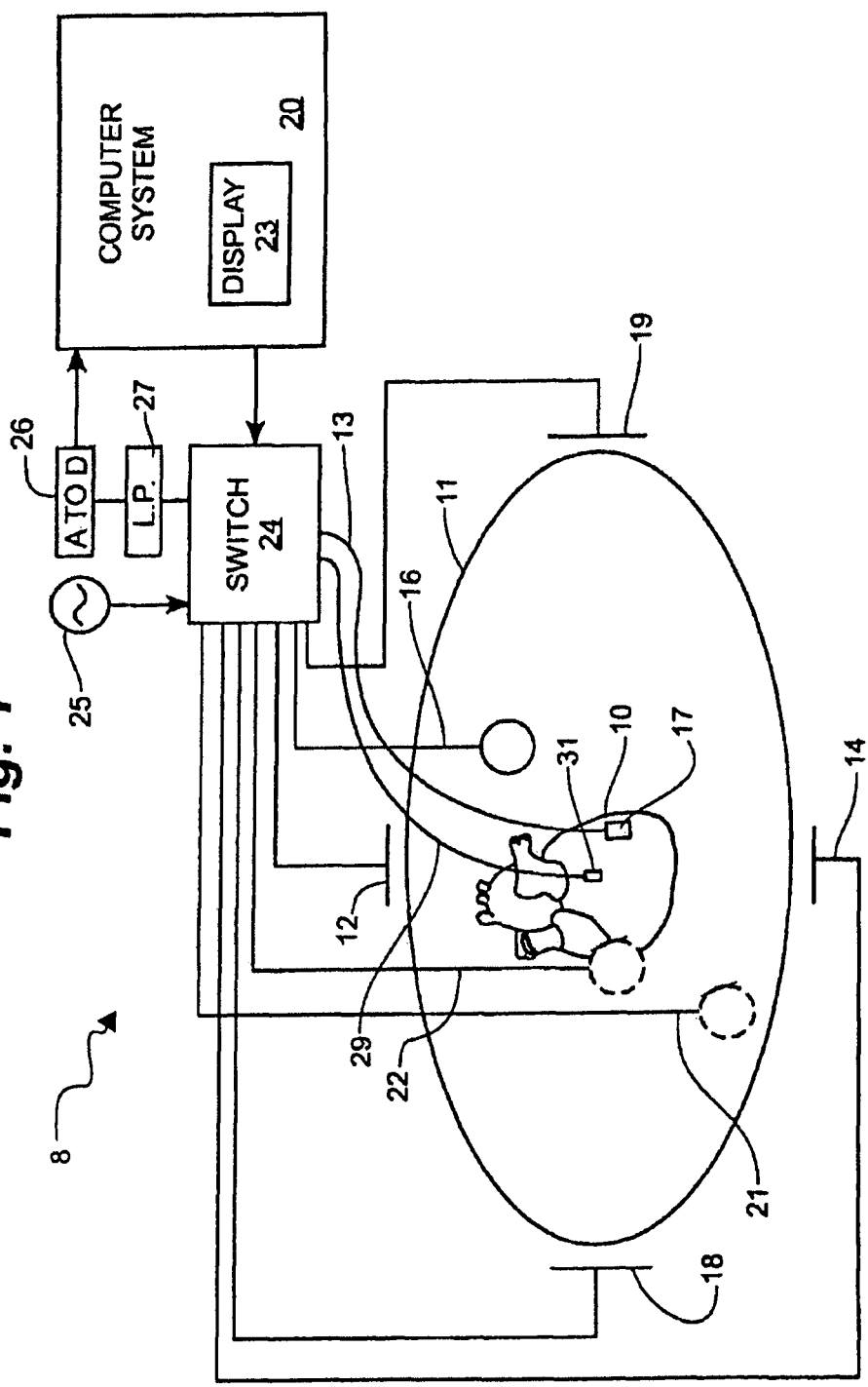
FIG. 1 is a schematic diagram of a localization system utilized in an electrophysiology study.

FIG. 1 shows a schematic diagram of a localization system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. System 8 can be used, for example, to create an anatomical model of the patient's heart 10 using one or more electrodes. System 8 can also be used to measure electrophysiology data at a plurality of points along a cardiac surface, and store the measured data in association with location information for each measurement point at which the electrophysiology data was measured, for example to create a diagnostic data map of the patient's heart 10. As one of ordinary skill in the art will recognize, and as will be further described below, localization system 8 determines the location of objects, typically within a three-dimensional space, and expresses those locations as position information determined relative to at least one reference.

For simplicity of illustration, the patient 11 is depicted schematically as an oval. Three sets of surface electrodes (e.g., patch electrodes) are shown applied to a surface of the patient 11, defining three generally orthogonal axes, referred to herein as an x-axis, a y-axis, and a z-axis. The x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional electrocardiogram (ECG) system leads in place. This ECG information is available to the system 8, although not illustrated in FIG. 1.

A representative catheter 13 having at least one electrode 17 (e.g., a distal electrode) is also shown. This representative catheter electrode 17 is referred to as the "roving electrode," "moving electrode," or "measurement electrode" throughout the specification. Typically, multiple electrodes on catheter 13, or on multiple such catheters, will be used. In one embodiment, for example, localization system 8 may comprise up to sixty-four electrodes on up to twelve catheters disposed within the heart and/or vasculature of the patient. Of course, this embodiment is merely exemplary, and any number of electrodes and catheters may be used within the scope of the present invention.

Figure 2:
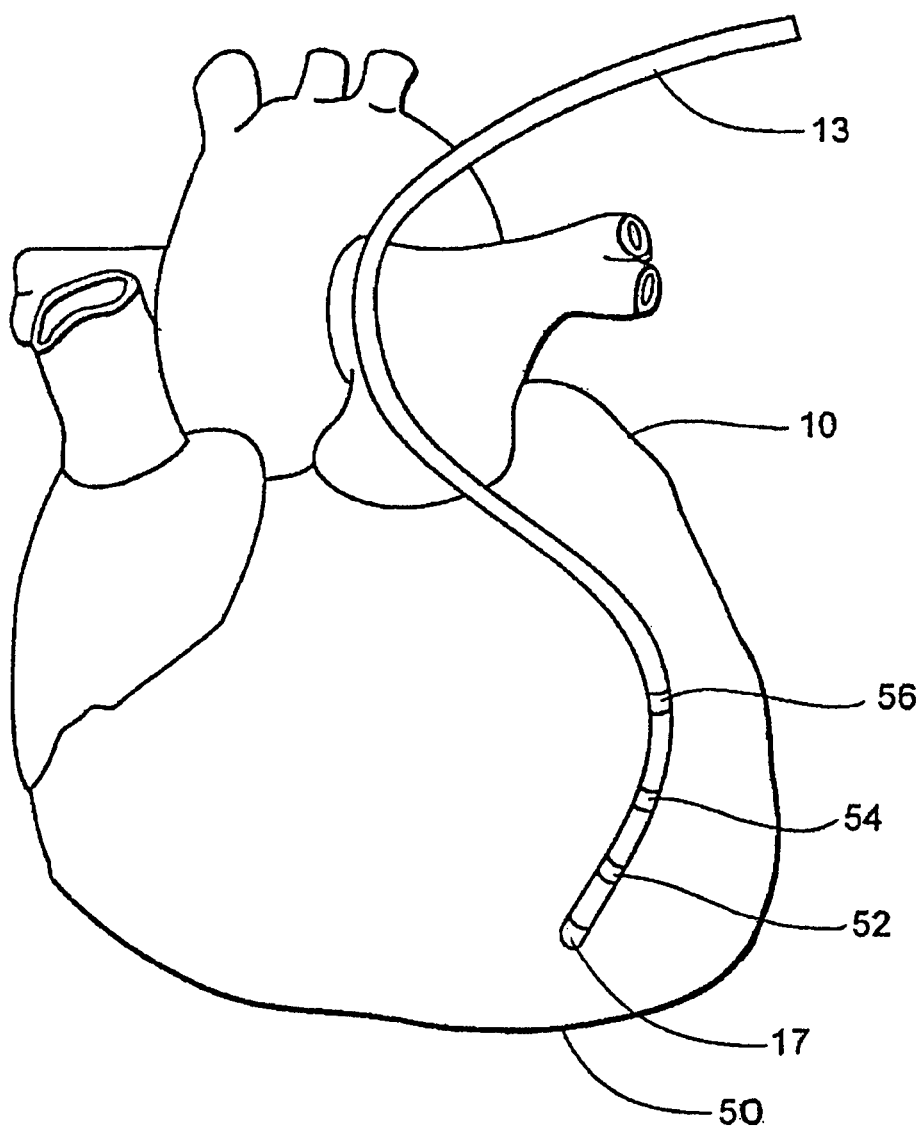
FIG. 2 depicts an exemplary catheter used in an electrophysiology study.

For purposes of this disclosure, an exemplary catheter 13 is shown in FIG. 2. In FIG. 2, catheter 13 extends into the left ventricle 50 of the patient's heart 10. Catheter 13 includes electrode 17 on its distal tip, as well as a plurality of additional measurement electrodes 52, 54, 56 spaced along its length. Typically, the spacing between adjacent electrodes will be known, though it should be understood that the electrodes may not be evenly spaced along catheter 13 or of equal size to each other. Since each of these electrodes 17, 52, 54, 56 lies within the patient, location data may be collected simultaneously for each of the electrodes by localization system 8.

Returning now to FIG. 1, an optional fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrodes (e.g., electrodes 17, 52, 54, 56), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to the multiplex switch 24, and the pairs of surface electrodes are selected by software running on a computer 20, which couples the surface electrodes to a signal generator 25. The computer 20, for example, may comprise a conventional general-purpose computer, a special-purpose computer, a distributed computer, or any other type of computer. The computer 20 may comprise one or more processors, such as a single central processing unit (CPU), or a plurality of processing units, commonly referred to as a parallel processing environment, which may execute instructions to practice the various aspects of the present invention described herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Additionally, such non-orthogonal methodologies add to the flexibility of the system. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The roving electrodes 17, 52, 54, 56 placed in the heart 10 are exposed to the field from a current pulse and are measured with respect to ground, such as belly patch 21. In practice the catheters within the heart may contain more or fewer electrodes than the four shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which localization system 8 measures positions. Data sets from each of the surface electrodes, the internal electrodes, and the virtual electrodes may all be used to determine the location of the roving electrodes 17, 52, 54, 56 within heart 10.

The measured voltages may be used to determine the location in three-dimensional space of the electrodes inside the heart, such as roving electrodes 17, 52, 54, 56, relative to a reference location, such as reference electrode 31. That is, the voltages measured at reference electrode 31 may be used to define the origin of a coordinate system, while the voltages measured at roving electrodes 17, 52, 54, 56 may be used to express the location of roving electrodes 17, 52, 54, 56 relative to the origin. Preferably, the coordinate system is a three-dimensional (x, y, z) Cartesian coordinate system, though the use of other coordinate systems, such as polar, spherical, and cylindrical coordinate systems, is within the scope of the invention.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described in U.S. Patent Application Publication No. 2004/0254437, which is hereby incorporated herein by reference in its entirety. The electrode data may also be used to compensate for changes in the impedance of the body of the patient as described in co-pending U.S. patent application Ser. No. 11/227,580, filed on 15 Sep. 2005, which is also incorporated herein by reference in its entirety.

In summary, the system 8 first selects a set of surface electrodes and then drives them with current pulses. While the current pulses are being delivered, electrical activity, such as the voltages measured at least one of the remaining surface electrodes and in vivo electrodes, is measured and stored. Compensation for artifacts, such as respiration and/or impedance shifting, may be performed as indicated above.

In a preferred embodiment, the localization/mapping system is the EnSite NavX™ navigation and visualization system of St. Jude Medical, Atrial Fibrillation Division, Inc., which generates the electrical fields described above. Other localization systems, however, may be used in connection with the present invention, including for example, the CARTO navigation and location system of Biosense Webster, Inc., or the AURORA® system of Northern Digital Inc., both of which utilize magnetic fields rather than electrical fields. The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

The fields generated by localization system 8, whether an electrical field (e.g., EnSite NavX™), a magnetic field (e.g., CARTO, AURORA®), or another suitable field, may be referred to generically as "localization fields," while the elements generating the fields, such as surface electrodes 12, 14, 16, 18, 19, and 22 may be generically referred to as "localization field generators." As described above, surface electrodes 12, 14, 16, 18, 19, and 22 may also function as detectors to measure the characteristics of the localization field (e.g., the voltages measured at roving electrodes 17, 52, 54, 56). Though the present invention will be described primarily in the context of a localization system that generates an electrical field, one of ordinary skill in the art will understand how to apply the principles disclosed herein in other types of localization fields (e.g., by replacing electrodes 17, 52, 54, 56 with coils to detect different components of a magnetic field).

Localization system 8 may be provided with a three-dimensional lookup table that includes reference data correlating locations of an object within the localization field with measurements made by the localization system when the object is at various locations within the localization field. For example, as described above, the voltages measured at roving electrodes 17, 52, 54, 56 within the electrical field generated by surface electrode pairs 12/14, 18/19, and 16/22 may be utilized to determine the location of electrodes 17, 52, 54, 56 within the localization field, such that the reference data in the lookup table may include information relating voltage readings to physical location within the localization field. In effect, the lookup table defines a three-dimensional coordinate system for the localization field, including a plurality of reference points (e.g., the cells or nodes of the lookup table) that serve as references for defining or identifying the observed location of an object located within the localization field. In some embodiments of the invention, the three-dimensional lookup table, and therefore the three-dimensional coordinate system, is created by a modeling processor, which may be incorporated within computer 20.

Initially, the lookup table may include predicted reference data for a completely homogenous localization field. Such a lookup table is illustrated (in two dimensions) in FIG. 3. For purposes of illustration only, the lookup table assumes that 9 volts are applied across the surface electrodes of the x-axis (patch electrodes 12, 14) and the y-axis (patch electrodes 18, 19), and that the surface electrodes are each separated by a distance of 9 units, such that a change of 1 volt is equivalent to a movement of 1 unit. Further, the lookup table assumes that the origin (0,0), defined, for example, by reference electrode 31, experiences a voltage of 3 volts on the x-axis and 5 volts on the y-axis. Voltages greater than the voltage measured at reference electrode 31 are defined as positive, while voltages less than the voltage measured at reference electrode 31 are defined as negative. Each entry within the lookup table (e.g., each cell or node of the lookup table) defines a reference point for the coordinate system relative to which localization system 8 measures positions of objects within the localization field. Though only integer values are depicted in the lookup table of FIG. 3, it is contemplated that the lookup table utilized in practicing the invention may have additional detail (that is, the axes of the lookup table may be graduated in any interval). Of course, it is also contemplated that intermediate values (that is, values not corresponding exactly to a cell within the lookup table) may be determined through interpolation, preferably utilizing an interpolation function that is continuous between nodes of the lookup table.

As one of ordinary skill in the art should recognize, contrary to the assumption utilized to originally populate the nodes of the three-dimensional lookup table, the localization field generated by localization system 8 may not be perfectly homogeneous. The predicted reference data used to initially populate the lookup table may therefore be imprecise, and may introduce error into the measured positions of roving electrodes 17, 52, 54, 56 or another object within the localization field. It is desirable to correct for these inhomogeneities so as to minimize measurement error, thereby improving the accuracy and precision of localization system 8.

After placing the catheter into the localization field, localization system 8 may be utilized to determine the location of each of the plurality of electrodes 17, 52, 54, 56 based on the data in the lookup table. The locations of electrodes 17, 52, 54, 56, as determined by the reference data in the lookup table, may then be used to calculate an observed distance between pairs of electrodes, and preferably between pairs of adjacent electrodes such as electrodes 17 and 52.

For example, suppose localization system 8 measures a voltage of 7 volts on the x-axis and 6 volts on the y-axis at electrode 17, and a voltage of 7 volts on the x-axis and 8 volts on the y-axis at electrode 52. The lookup table, as originally populated for a homogenous localization field, indicates that electrode 17 is located at coordinates (4,1), while electrode 52 is located at coordinates (4,3). The observed distance between electrodes 17 and 52 is therefore 2 units, as given by the equation $d=\sqrt{(x_1-x_2)^2+(y_1-y_2)^2}$, where d is the distance between two coordinate points $(x_1, y_1)$ and $(x_2, y_2)$.

As described above, the actual distance between electrodes 17 and 52 is known. The observed distance between electrodes 17 and 52 may differ from the actual distance due to inhomogeneities in the localization field. Accordingly, an error processor, which may be part of computer 20, preferably compares the observed distance to the actual distance in order to determine and output an error signal. The error signal, in turn, may be used to adjust the reference data in the three-dimensional lookup table in order to more accurately measure the spacing of electrodes 17, 52, 54, 56. A correction processor, which may be incorporated in computer 20, and which is preferably coupled to the modeling processor and the error processor, may adjust the reference data to reduce the error signal (that is, to reduce the difference between the observed distance and the actual distance).

It should be understood that, though electrodes 17 and 52 are used herein as an example, the error signal preferably incorporates information from all electrodes 17, 52, 54, 56 as catheter 13 moves through the localization field over time, thereby providing a plurality of observed distances between pairs of electrodes that may be compared to the actual distances between those electrodes. This may be done in real-time or on pre-recorded data.

In some embodiments of the invention, a Kernel function is used to adaptively update the reference data in the three-dimensional lookup table. Preferably, the Kernel function is a decay function, in that updates to the reference data diminish in magnitude as the adjustment point increases in distance from the locations of the plurality of electrodes. That is, the reference point or node in the lookup table closest to the observed coordinate will be updated the most, those reference points or nodes in the lookup table directly adjacent to the observed coordinate will be updated next-most, and so on; those reference points or nodes in the lookup table furthest from the observed coordinate will be updated the least, or potentially not at all.

One suitable Kernel function is a derivative of a Gaussian curve, and may be given by the general formula $$K(x) = axe^{-\frac{x^2}{2\sigma^2}}.$$

Figure 4:
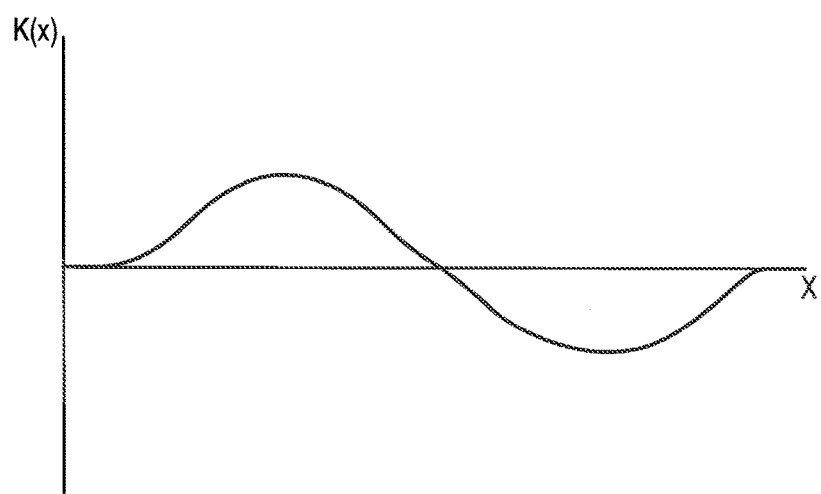
FIG. 4 illustrates a Kernel function.

This Kernel function is illustrated in FIG. 4, and has both positive and negative lobes that decay smoothly to zero as distance from the center of the lobe increases. It is contemplated, however, that any Kernel function having both a positive lobe and a negative lobe, each of which decays smoothly to zero as distance from the center of the lobe increases, may be utilized to practice the present invention.

Thus, for example, if the observed distance between electrodes is less than the known distance between electrodes, the error signal is negative, and the distance separating reference points within the coordinate system may be increased (e.g., the localization field may be stretched). Similarly, if the observed distance between electrodes is greater than the known distance between electrodes, the error signal is positive, and the distance separating reference points within the coordinate system may be reduced (e.g., the localization field may be contracted).

Figure 5A:
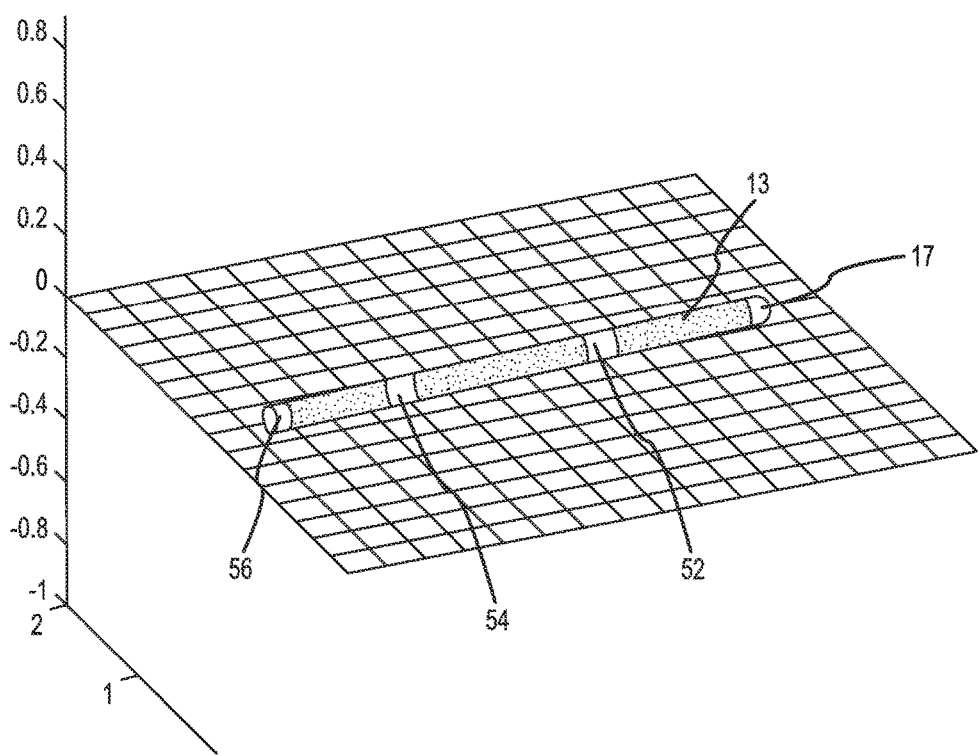
FIG. 5a illustrates a catheter as observed by a localization system assumed to be homogeneous.
Figure 5B:
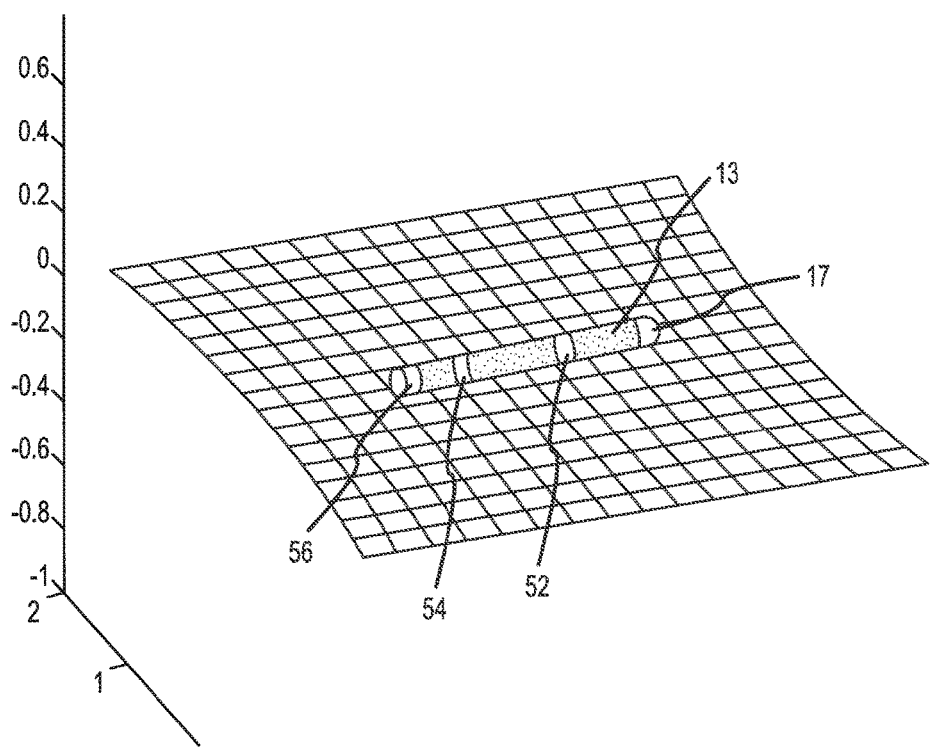
FIG. 5b illustrates the catheter of FIG. 5a as observed after an iteration of updates has been performed on the reference points for the localization system.

The latter case is illustrated in FIGS. 5a and 5b. FIG. 5a illustrates catheter 13 and electrodes 17, 52, 54, 56 as measured within the localization field created by localization system 8. The localization field is illustrated as a grid. The observed distance between electrodes 17 and 52 is about 4 units, the observed distance between electrodes 52 and 54 is about 5 units, and the observed distance between electrodes 54 and 56 is about 3.5 units. Assume, however, that the known distance between electrodes is only 1 unit, such that the observed values are too large (e.g., catheter 13 appears to have stretched beyond its known dimensions). The Kernel function will accordingly update the reference data within the three-dimensional lookup table to effectively contract the localization field. As shown in FIG. 5b, which represents the localization field of FIG. 5a after a single iteration of the Kernel function, the reference points (e.g., the grid) have been contracted, and the entries within the lookup table have been updated, such that the observed distance between electrodes 17 and 52 is about 2.5 units, the observed distance between electrodes 52 and 54 is about 3 units, and the observed distance between electrodes 54 and 56 is about 2 units.

As should be clear from the foregoing discussion, a single iteration of the Kernel function may not account for all inhomogeneities in the localization field. Preferably, comparatively small adjustments to the reference data are made during each iteration of the Kernel function to approach an optimal solution with a diminishingly small error signal. It is also contemplated that these iterations may be performed in real-time while catheter 13 is moved within the patient's heart 10, for example while collecting a plurality of geometry points from which a cardiac surface model will be generated, and the geometry points so collected may also be updated along with the reference data in the three-dimensional lookup table.

After a sufficient number of iterations of the Kernel function have been performed, the three-dimensional lookup table will have been updated to approach an optimal solution with a diminishingly small error signal. An object may then be placed in the localization field, and the location of the object may be accurately and precisely determined using the adjusted data in the three-dimensional lookup table.

More generally, the present invention may be utilized to locate an object in a defined space, even if that object lacks elements having a known spacing as would typically be the case for electrodes 17, 52, 54, 56. As described above, the localization field may have a defined three-dimensional coordinate system including a plurality of reference points that serve as references for defining an observed location of an object within the localization field. A calibration tool or object (for example, catheter 13) having a plurality of calibration elements (for example, electrodes 17, 52, 54, 56) spaced at known distances may be placed into the localization field. Reference information, such as position information for each of the calibration elements, may then be received relative to the three-dimensional coordinate system, and an observed spacing distance may be calculated for at least two of the calibration elements. A calibration signal may then be generated based on a comparison of the observed spacing distance and the known spacing distance. An object may then be placed in the localization field proximate the calibration tool, and the calibration signal may be used to determine the location of the object in the localization field.

As described above, at least some of the plurality of reference points may be adaptively processed with a Kernel function to create a revised three-dimensional coordinate system that reduces, and, after a sufficient number of iterations, diminishes towards zero, the difference between the observed spacing distance and the known spacing distance. An object may be placed within the localization field and its position determined relative to the revised three-dimensional coordinate system.

Although several embodiments of this invention have been described above with a certain degree of particularity, those skilled in the art could make numerous alterations to the disclosed embodiments without departing from the spirit or scope of this invention. For example, the functions of the various processors described herein (e.g., the modeling processor, the error processor, and the correction processor) may be incorporated into one or more processors within one or more computer systems without departing from the spirit and scope of the present invention.

In addition, though the invention has been described in connection with electric or magnetic localization fields, it is contemplated that the invention could also be practiced in connection with an imaging system, such as fluoroscopic imaging, intercardiac echo, magnetic resonance, or the like used for catheter navigation. These imaging systems are regarded as within the meaning of the term "localization field" as used herein.

Further, though the invention has been described as utilizing an iteratively-updated lookup table that relates measurements made by the localization system with locations of an object within the localization field, other methodologies are within the spirit and scope of the present invention. For example, algebraic methods, including the use of weighted functions, may be used in place of the lookup table; inhomogeneities in the localization field may be compensated for by adjusting the relative weights of the functions. Similarly, neural network or other machine learning techniques may be utilized.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method for determining a location of an object in a three-dimensional localization field created by a localization computer system, comprising:
   providing a catheter having a plurality of electrodes, each of which is spaced from an adjacent electrode by a known electrode spacing distance;
   providing a three-dimensional lookup table for use by the localization computer system, wherein the table comprises reference data correlating locations of an object within the localization field with measurements made by the localization computer system when the object is at different locations;
   placing the catheter into the localization field;
   using the localization computer system to determine the location of each of the plurality of electrodes based on the reference data in the three-dimensional lookup table;
   calculating, with the localization computer system, an observed distance between each pair of adjacent electrodes from the determined locations of each of the plurality of electrodes;
   determining, with the localization computer system, an error signal by comparing the observed distance between at least one pair of adjacent electrodes to the known electrode spacing between the at least one pair of adjacent electrodes; and
   adjusting, with the localization computer system, the reference data in the three-dimensional lookup table based on the error signal to more accurately measure the spacing of the electrodes.

2. The method of claim 1, wherein adjusting the reference data in the three-dimensional lookup table based on the error signal comprises using a Kernel function to adaptively update the reference data in the three-dimensional lookup table.

3. The method of claim 2, wherein the Kernel function is a decay function, in that updates to the reference data diminish in magnitude as the adjustment point increases in distance from the locations of the plurality of electrodes.

4. The method of claim 2, wherein the Kernel function is a derivative of a Gaussian curve.

5. The method of claim 4, wherein the Kernel function has a general form $$K(x) = axe^{-\frac{x^2}{2\sigma^2}}.$$

6. The method of claim 1, further comprising placing a first object in the localization field and determining, with the localization computer system, the location of the first object using the adjusted data in the three-dimensional lookup table.

7. The method of claim 1, wherein the reference data comprises information that relates voltage readings to physical location within the localization field.

8. The method of claim 1, wherein providing a three-dimensional lookup table comprises generating a three-dimensional lookup table by predicting reference data for a perfectly homogeneous localization field.

9. A method for locating an object in a defined space, comprising:
   providing a calibration object having a plurality of calibration elements spaced at known spacing distances;
   defining, with a localization computer system, a three-dimensional coordinate system for a localization field, the coordinate system comprising a plurality of reference points which serve as references for defining an observed location of an object located in the localization field;
   placing the calibration object into the localization field;
   generating, with the localization computer system, a lookup table for use in conjunction with the three-dimensional coordinate system, wherein the table comprises reference data that can be used to correlate locations of an object within the localization field with observed locations when the object is at different locations within the localization field;
   receiving, with the localization computer system, reference information from the lookup table relative to the three-dimensional coordinate system, the reference information providing position information for each of the calibration elements;
   calculating, with the localization computer system, an observed spacing distance for at least two of the calibration elements;
   generating, with the localization computer system, a calibration signal based on a comparison of the observed spacing distance and the known spacing distance;
   adjusting, with the localization computer system, the reference data in the lookup table based on the calibration signal to more accurately measure the spacing of the electrodes;
   placing an object in the localization field;
   receiving, with the localization computer system, adjusted reference information from the lookup table relative to the three-dimensional coordinate system, the reference information providing position information for each of the object placed in the localization field; and using the adjusted reference data in the lookup table to determine, with the localization computer system, the location of the object placed in the localization field.

10. The method of claim 9, further comprising adaptively processing, with the localization computer system, at least some of the plurality of reference points of the three-dimensional coordinate system with a Kernel function to create a revised three-dimensional coordinate system such that a difference between the observed spacing distance and the known spacing distance is reduced.

11. The method of claim 10, wherein the step of adaptively processing at least some of the plurality of reference points of the three-dimensional coordinate system comprises:

reducing a distance separating at least two reference points of the three-dimensional coordinate system when the observed spacing distance is greater than the known spacing distance; and increasing a distance separating at least two reference points of the three-dimensional coordinate system when the observed spacing distance is less than the known spacing distance.

12. The method of claim 10, wherein the step of adjusting the reference data in the lookup table comprises:

adjusting the reference data in the lookup table based on the calibration signal and based on the revised three-dimensional coordinate system.

13. A localization computer system with error correction for inhomogeneous localization fields for use with a calibration object having a plurality of calibration elements spaced at known spacing distances, said system comprising:

at least one localization field generator for creating a three-dimensional localization field that can be used for determining a location of an object within the three-dimensional localization field;

at least one detector to measure the characteristics of the three-dimensional localization field generated by the at least one localization field generator;

the system configured to create a three-dimensional coordinate system for the localization space and a three-dimensional look up table comprising reference data correlating locations of an object within the three-dimensional localization field with measurements made by the localization system when the object is at different locations within the three-dimensional localization field;

the system further configured to determine differences between the known spacing distances of the calibration elements and measured distances between the calibration elements, where the differences are a function of inhomogeneous localization fields;

the system further configured to adjusts the reference data in the look up table to minimize the differences between the known spacing distances of the calibration elements and measured distances between the calibration elements; and wherein the system uses a Kernel function to adaptively update the reference data in lookup table.

14. The system of claim 13, wherein the Kernel function is a decay function.

15. The method of claim 13, wherein the Kernel function is a derivative of a Gaussian curve.

16. The system of claim 13, wherein the system comprises at least three detectors and wherein the system creates a three-dimensional lookup table in which the reference points are associated with measurement values to be measured by the at least three detectors.

17. The system of claim 13, wherein:

the at least one localization field generator comprises three pairs of electrodes spaced along three axes, wherein the three pairs of electrodes create three electric fields that can be used to determine location of an object within a localization space;

the at least one detector measures a voltage level associated with each of the three electric fields;

the system creates a three-dimensional coordinate system comprising a three-dimensional lookup in which the reference points of the coordinate system are associated with measurement values for each of the three electric fields as measured by the at least one detector; and the computer adjusts for inhomogeneities in the three electric fields.

18. The system of claim 13, wherein the localization field is a magnetic field, and wherein the at least one detector comprises three coils to detect different components of the magnetic field.

* * * * *